United States Patent [19]

Sanidas

[11] 4,368,733
[45] Jan. 18, 1983

[54] INVALID FECES COLLECTING AND EXAMINATION DEVICE FOR MEDICAL STUDY OF STOOL AND EXAMINATION OF THE GENITALIA

[76] Inventor: John D. Sanidas, 101 Dexter St., Denver, Colo. 80220

[21] Appl. No.: 849,475

[22] Filed: Nov. 7, 1977

[51] Int. Cl.³ .............................................. A61F 5/44
[52] U.S. Cl. ................................... 128/283; 128/286
[58] Field of Search ............. 128/283, 286, 2 F, 275, 128/132 D, 292, 295; 4/177 R, 111, 112, 114, 134–135, 137, 138, 144.1–144.4, 185 S

[56] References Cited

U.S. PATENT DOCUMENTS

| 77,937 | 5/1868 | Welling | 4/112 |
|---|---|---|---|
| 1,227,399 | 5/1917 | Wendt | 128/275 |
| 2,837,095 | 6/1958 | Stevenson | 128/284 |
| 2,900,979 | 8/1959 | Bishop | 128/283 |
| 3,034,131 | 5/1962 | Lent | 128/25 R UX |
| 3,316,911 | 5/1967 | Barr | 128/295 |
| 3,421,506 | 1/1969 | Webb et al. | 128/286 |
| 3,561,439 | 2/1971 | Bayer | 128/132 D |
| 3,577,989 | 5/1971 | Anderson | 128/283 |
| 3,677,266 | 7/1972 | Green | 128/132 D |
| 3,849,811 | 11/1974 | Cyll | 128/295 |

FOREIGN PATENT DOCUMENTS

| 818238 | 10/1951 | Fed. Rep. of Germany | 4/144.3 |
|---|---|---|---|
| 1272 | of 1882 | United Kingdom | 128/295 |

Primary Examiner—Kyle L. Howell
Assistant Examiner—C. W. Shedd
Attorney, Agent, or Firm—W. Britton Moore

[57] ABSTRACT

Disposable type body encircling device having a front opening for examination access to the genitalia and a rearwardly disposed anal opening adhesively adhered around the anus. A funnel shaped strut reinforced tubular chute portion depends from the anal area and is formed with an open and sealable discharge end for removable attachment to the upper end of a disposable bag so that feces is droppable and collectable therein without soiling the patient and for visual inspection thereof. The bag may be detached from the chute portion to enable rectal tests and examinations to be made therethrough, and for emptying, cleaning, and/or replacement thereof when needed, permitting temporary sealing of the chute when the patient is lying on one side, or becomes ambulatory.

6 Claims, 11 Drawing Figures

INVALID FECES COLLECTING AND EXAMINATION DEVICE FOR MEDICAL STUDY OF STOOL AND EXAMINATION OF THE GENITALIA

This invention relates to a disposable type diaper like having a front access opening to the genitalia and a rear anal opening for adhesive adherence around the anus, and a tubular strut reinforced chute portion depending therefrom for removable attachment to a feces collecting and examination bag.

Heretofore, it has been proposed to provide elimination trapping diapers and the like for incontinent persons, such as U.S. Pat. Nos. to Wiley 395,411, Lewis 1,915,324, Loveret 3,532,093, and Anderson 3,577,989, but these devices are not suitable for hospital use to enable bed-ridden patients to dispose of their feces, separate from urinary discharges, so that observation of the former may determine the presence of blood, pus, mucus, diarrhea, etc., in addition to enabling rectal tests to be made and affording access to the genitalia without disturbing the patient.

The principal object of the present invention is to provide a disposable type body encircling diaper like device having a rearwardly disposed anal opening adhesively secured around the anus and formed with a depending tubular chute having its discharge end removably attached to a disposable bag so that feces is droppable and collectable therein without disturbing the patient.

Another object is to provide a disposable type body encircling diaper like device having a front access opening to the genitalia and an anal opening spaced therefrom and adhesively secured around the anus and formed with a strut reinforced tubular chute removably attached to a disposable bag so that feces are collectable therein and rectal examinations may be made through the chute when disconnected from the bag.

A further object is the provision of a body encircling diaper like device for use with a patient disposed on an apertured-mattress hospital bed, and/or sitting on an apertured-seat chair, and wherein the anus-attachable chute thereof and the feces collecting bag depend through the mattress or chair opening and the bag is either floor or bed frame supported to avoid discomfort to the patient.

Still another object is the provision of a body encircling disposable diaper like device having an anal opening surrounded by an adhesive area with a protective covering thereon, and wherein removal of the covering permits the adhesive area to be attached securely to the buttocks around the anus.

A still further object is to provide a body encircling disposable diaper like device having an anal opening and an inverted, strut-reinforced, funnel-shaped chute depending therefrom to enable feces to drop therethrough without sticking thereto.

Another object is the provision of a body encircling disposable diaper like device wherein the upper end of the depending chute at the anal opening has flexible but firm struts extending therebelow and outwardly thereof to prevent the enlarged upper end of the chute from collapsing and enable passage of the feces therethrough.

A further object is to provide a body encircling diaper like device having a front opening affording access to the vagina or penis and scrotum for examination by medical personnel, and enabling insertion of catheters, vaginal tampons, Pap smears, and surgical procedures, without removing the diaper from the patient, or contacting and being contaminated by the feces.

Still another object is the provision of a body encircling diaper like device having a feces discharging chute removably connected to a feces collecting bag, whereby upon removal of the latter the discharge end of the chute may be sealed to render the patient ambulatory.

These and other objects and advantages will be apparent as the specification is considered with the accompanying drawings, wherein FIG. 1 is a perspective view of a patient reclining on a regular hospital bed, with the diaper and feces collecting bag depending therefrom;

Figure 1:
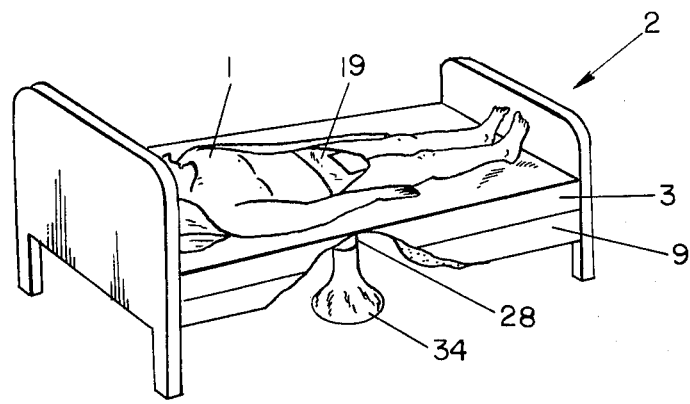
Figure 7:
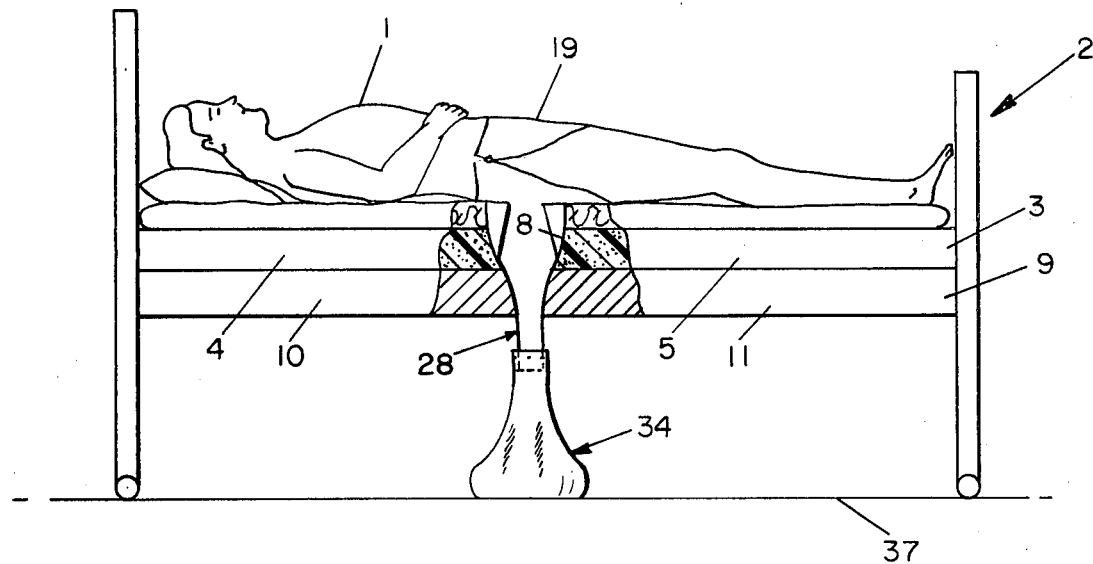
FIG. 7 is a side elevation, partly in section, showing a patient disposed on a regular hospital bed, and the chute and collecting bag depending through mattress and box spring openings.
Figure 9:
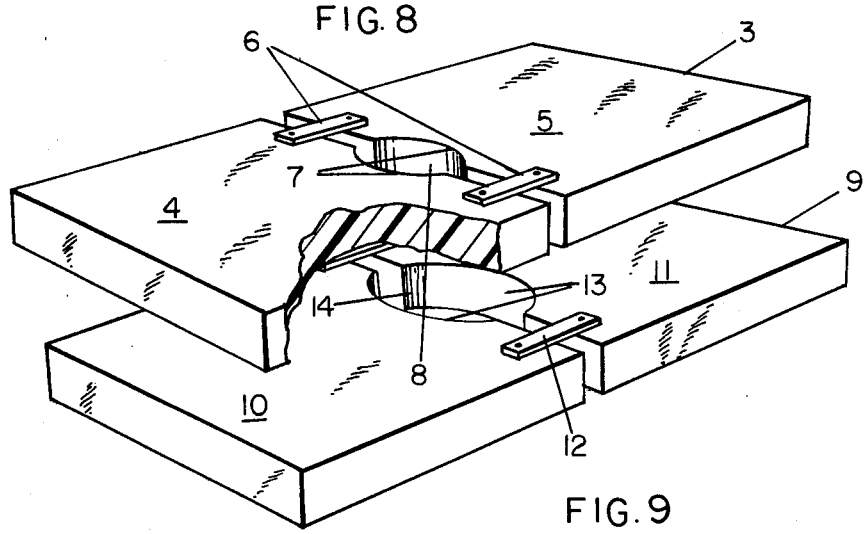
FIG. 9 is a perspective view, partly in section, of a two-part apertured mattress and box springs.

Referring more particularly to the drawings, wherein similar reference characters designate like parts throughout the several views, the diaper like device of this invention is suitable for use with a patient 1 reclining on a conventional hospital bed 2, shown in FIGS. 1 and 7, having a mattress 3 divided into two sections 4–5, best shown in FIG. 9, with the sections interconnected by suitable spaced straps or the like, 6. The mating inner ends of the mattress sections are arcuately recessed, as at 7, to provide a generally circular opening 8 therethrough. Two-part box springs 9 having two sections 10–11, interconnected by spaced straps 12, are similar arcuately recessed, as at 13, to provide circular opening 14. When assembled on the bed, mattress 3 is superposed on box springs 9 so that openings 8 and 14 are aligned, as best shown in FIG. 7.

Figure 8:
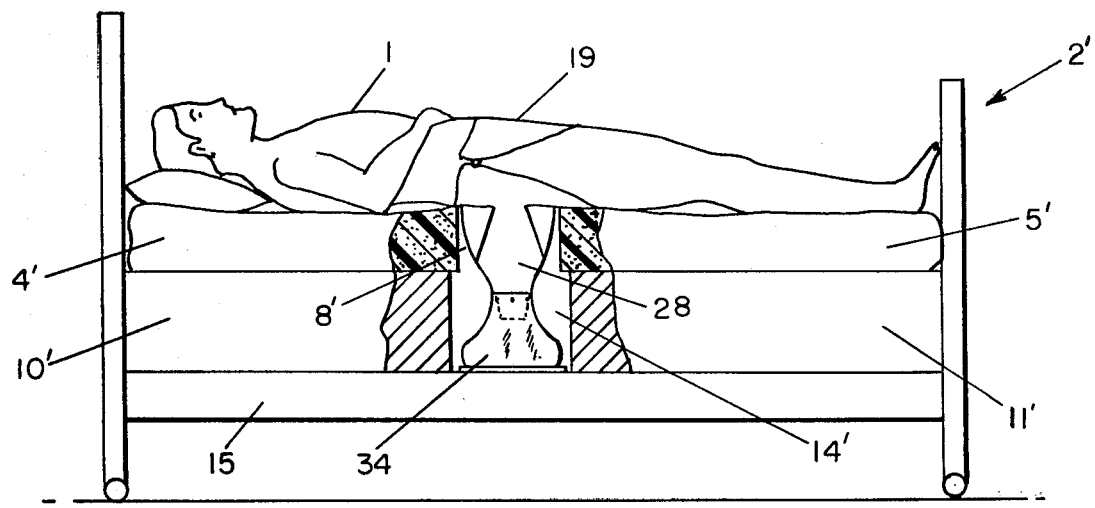
FIG. 8 is a side elevation, similar to FIG. 7, showing an electrically controlled hospital bed.

The diaper like device is also usable with an electrically controlled bed 2', as shown in FIG. 8, wherein the mattress sections 4'-5' are superposed on box spring sections 10'-11' supported by an electrical housing frame 15 so that openings 8'-14' are aligned, as previously described.

Alternatively, a patient with a diaper like device thereon may be seated on a chair 16 with a circular opening 18 in the seat 17 thereof, as presently to be described more in detail.

Figure 2:
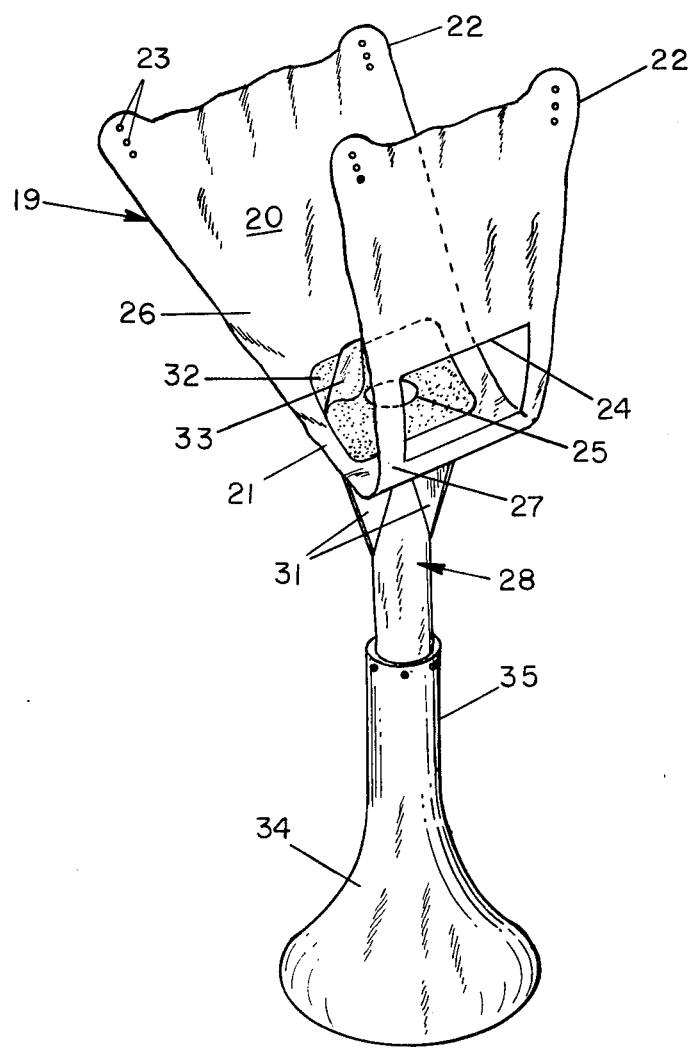
FIG. 2 is a perspective view of a disposable body encircling diaper, with the feces collecting bag in operative position, and showing the buttocks attaching adhesive area.

By referring to FIG. 2, a diaper like device 19 of some suitable soft flexible fabric, or plastic material so as to be disposable includes a generally flat panel 20 which is flared outwardly at opposing ends, as at 22, from a narrower midsection crotch area 21. The panel 20 is a sufficient length to enable encirclement of a human body, in the usual manner, and is provided with suitable snap fasteners or the like 23 at the corners thereof to enable the latter being overlapped and secured together, in an obvious manner as best shown in FIGS. 1, 7 and 8.

Panel 20 is formed with a generally rectangular opening 24 adjacent one end thereof, so that, when the diaper encircles and is secured to the wearer's waist, the opening will overlie and completely expose and afford access to the genitalia for examination thereof by medical personnel. Thus, when such procedures as insertion of catheters, vaginal tampons, vaginal examination and Pap smears, and various surgical procedures may be effected therethrough, without the diaper being removed or becoming contaminated by feces, as hereinafter will be apparent.

Spaced from opening 24 is a smaller circular opening 25, located in the anal area of the wearer, so that, when the narrower midsection 21 and upper side 26 of panel 20 is arranged in the buttock area, opening 25 will be aligned with and overlie the anus. Either formed integrally with panel 20, or otherwise suitably secured to the underside 27 thereof and encircling anus opening 25, is an inverted funnel-shaped tubular chute 28 depending therefrom and having an open lower discharge end 29. As the chute is preferably of the same material as the diaper, it will be somewhat flimsy and flexible, so the enlarged funnel-shaped upper end 30 thereof is reinforced with four exterior elongated struts 31, of some suitable semi-rigid plastic or metal material. Struts 31 are spacedly secured to the underside 27 of the panel, at points equally spaced from opening 24, and extend downwardly and inwardly to spaced points of juncture with the chute below the opening. The opposing ends of the angularly extending struts 31 may be embedded in the material of the diaper and chute, and sewn or otherwise suitably secured thereto, so as to reinforce and retain the upper end of the chute tubular and open, as shown in FIG. 2.

A generally rectangular area of upper side 26 of the panel, surrounding anal opening 25, is coated with a suitable tacky adhesive 32 having a suitable protective covering sheet 33 superposed thereon. Thus, when sheet 33 is peeled and removed from the adhesive area 32, and the upper side of panel 26 is flatly disposed over the crotch area and the buttocks are spread apart to exposed the anus, and with anal opening 25 aligned therewith, adhesive area 32 is pressed flatly against the secured to the anal area so that the flared ends of the panel may encircle and be secured to the wearer's waist.

Figure 3:
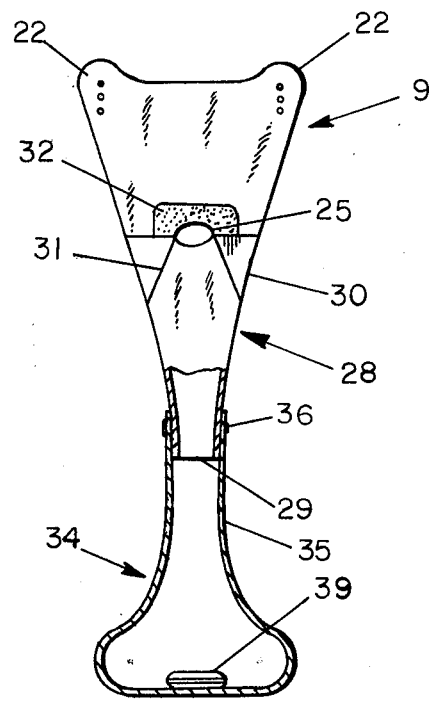
FIG. 3 is side view, partly in section, of the diaper, discharge chute, and collecting bag.
Figure 10:
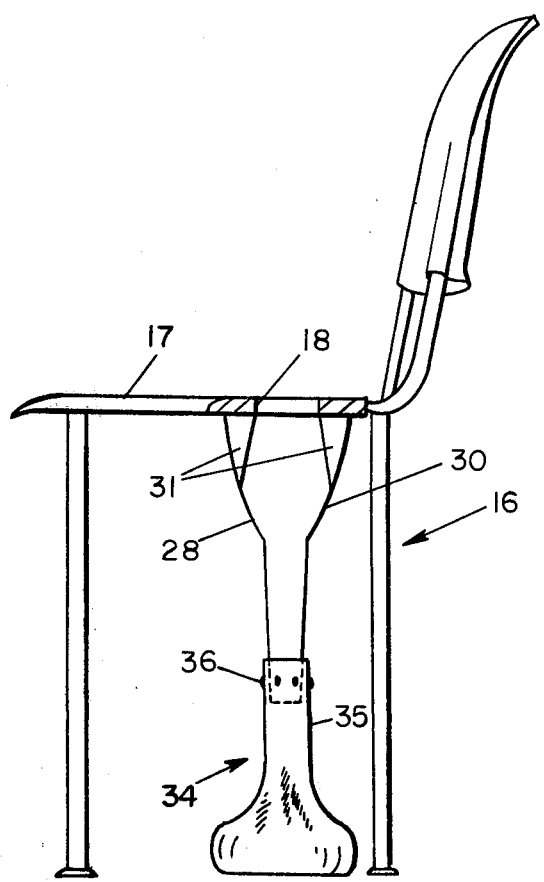
FIG. 10 is a side elevation, partly in section, of an apertured-seat chair and the position assumed by the chute and collecting bag when occupied by a patient.
Figure 11:
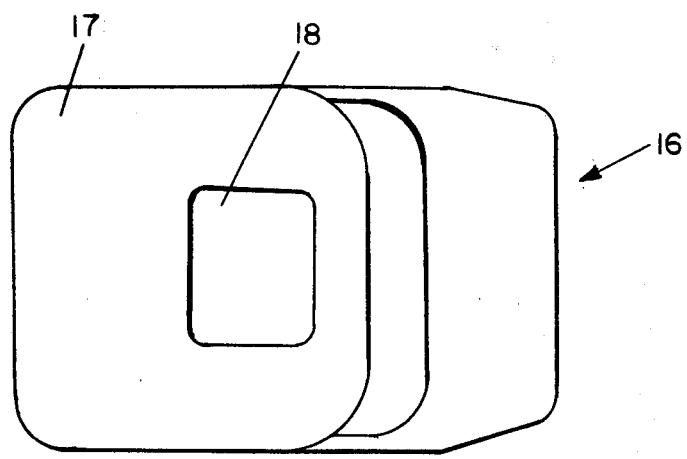
FIG. 11 is a top plan view of the chair of FIG. 10.

The lower discharge end 29 of chute 28 is sleeved within the reduced tubular upper end 35 of a collecting bag 34, of some suitable transparent plastic material to permit viewing of the contents therethrough. The respective lower and upper ends of the chute and bag are provided with suitable spaced connecting snaps 36 or the like to permit of their being removably interconnected, as shown in FIGS. 2 and 3. When so interconnected, the plastic collecting bag 34 will be an extension of and be vertically aligned with chute 28 and anal opening 25 so that feces discharged from the anus will drop downwardly through the chute and be collected in the bag. In the embodiment of FIGS. 1, 7 and 10, it will be noted that the bottom of the bag will rest upon and be supported by the floor 37 beneath bed 2 and the mattress and box spring openings thereof, or the chair 16 and seat opening therein. On the otherhand, in that of FIG. 8, the bottom of the collecting bag may be supported by the electric housing frame 15 and, thus, will be elevated above floor 37. As the snaps 36 are of the pull apart or snap type, and the collecting bag is supported by the floor or electric housing frame, in the event the patient suddently moves or lurches, in changing position on the bed, the snaps will disconnect to free the chute and the bag will remain upright so as not to upset its contents. The chute may thereafter be reattached to the bag when the patient assumes a more stable position, in an obvious manner.

Figure 5:
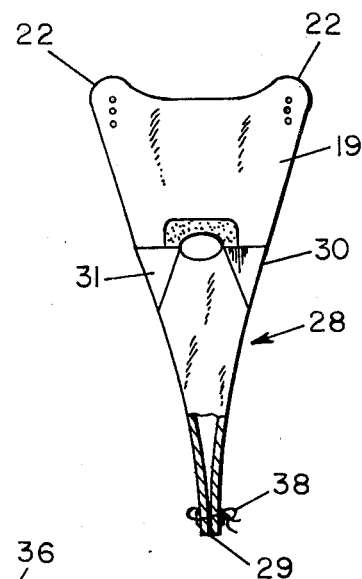
FIG. 5 is a side view, partly in section, of the diaper and discharge chute, with the collecting bag removed therefrom, and the chute sealed.
Figure 4:
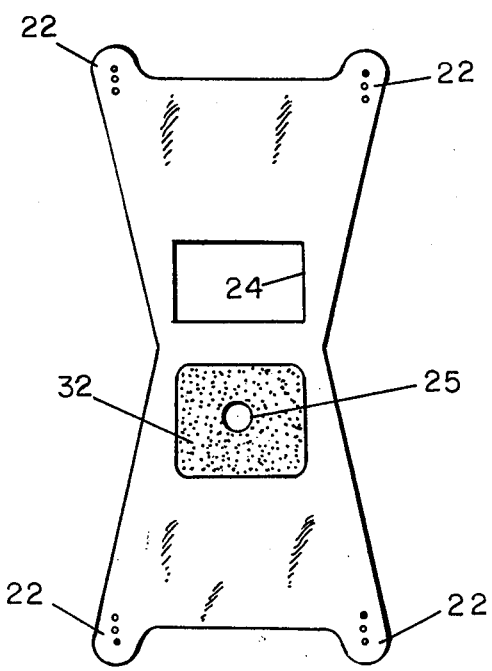
FIG. 4 is a top plan view of the diaper.
Figure 6:
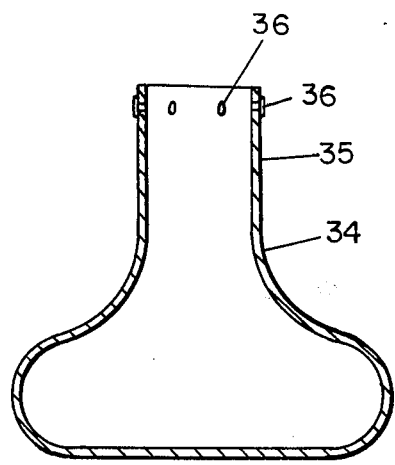
FIG. 6 is a vertical section through the collecting bag.

When the patient wishes to leave the bed or chair, or to lie on a side, the collecting bag 34 may be disconnected from chute 28, without any contamination to personnel, and the lower discharge end of the latter may be closed and sealed by some suitable means, e.g., a removable cord 38, as shown in FIG. 5. Any feces being when discharged will be collected in the chute for subsequent removal therefrom, or for collection by the bag when reattached thereto. It is also important to note that when the collecting bag is so disconnected, any required rectal tests and examinations by medical personnel may be effected through chute 28, with the diaper remaining attached to the wearer. For example, rectal temperatures may be taken, proctosigmoidoscopic, colonscopic, and rectal digital examinations made, in addition to the taking of anal specimens for parasites and their eggs, examination of the stool for any occult blood, and barium enema x-rays, etc. effected. In the event qualified personnel do not wish to disconnect the collecting bag when moving a patient a short distance, the bag may be supported by one or both hands, as the patient walks or is carried to another area.

If desired, a deodorant tablet or the like 39, as shown in FIG. 3, may be disposed in bag 34 to eliminate odor. Furthermore, it is important to understand that this diaper enables the feces only to be isolated so that all examinations may be done on this waste product without contamination or the liquefying effects of urine.

While a preferred embodiment of the present diaper has been shown and described, it is to be understood that various changes and improvements may be made without departing from the scope and spirit of the appended claims.

What I claim is:

1. An invalid feces collecting device for medical study of stool and for encircling attachment to a patient reclining on an apertured mattress hospital bed and/or apertured seat chair comprising a panel of soft flexible material having a reduced midsection and flared opposing ends, a generally rectangular opening in said panel and of a size for exposing and providing examination access to the genitalia when said ends encircle the patient, means on and for interconnecting said ends, a generally circular anal opening in said panel spaced from and reduced in size with respect to said genitalia examining opening and of a size to be alignable with the anus, funnel shaped tubular chute means of soft flexible material on and depending from said panel and surrounding said anal opening, said chute having an open discharge end, adhesive means on said panel adjacent and generally rectangularly surrounding said anal opening for conformably adhering said opening area to the area around the anus, and transparent collecting bag means removably interconnected by disconnectable connecting means to said chute discharge end whereby feces entering through said anal opening will be discharged through said chute means and collected by said bag means for visual inspection therethrough and laboratory study, and whereupon removal of said bag permits rectal examinations.

2. In a feces collecting diaper, according to claim 1, wherein a protective sheet means removably covers said adhesive area and is strippable therefrom.

3. In a feces collecting diaper, according to claim 1, wherein reinforcing elongated strut means secured to the underside of said panel and connected to said chute means retains the upper end of said chute means tubular and open.

4. In a feces collecting diaper, according to claim 1, wherein said chute means discharge end is sleeved within the upper end of said collecting bag means, and said respective ends have snap connecting means for removable pull apart interconnection of said chute means and said bag means.

5. In a feces collecting diaper, according to claim 1, wherein the discharge end of said chute means has means for closing and sealing said end when said collecting bag means is disconnected therefrom.

6. In a feces collecting diaper, according to claim 3, wherein said strut means is semi-rigid and includes spaced elongated struts connected to said panel adjacent to said anal opening and extending downwardly and outwardly therefrom for connection to said funnel-shaped upper end.

* * * * *